United States Patent [19]

Shutske et al.

[11] Patent Number: 4,487,934

[45] Date of Patent: Dec. 11, 1984

[54] METHOD OF PREPARING POLY-SUBSTITUTED ACYLBENZENES

[75] Inventors: Gregory M. Shutske, Somerset; Linda L. Setescak, Somerville, both of N.J.

[73] Assignee: Hoechst-Roussel Pharmaceuticals Inc., Somerville, N.J.

[21] Appl. No.: 157,916

[22] Filed: Jun. 6, 1980

[51] Int. Cl.³ .................. C07D 213/56; C07D 309/32; C07C 49/80
[52] U.S. Cl. ..................................... 546/314; 546/315; 549/72; 549/488; 524/795; 568/323; 568/324
[58] Field of Search ............... 568/323, 324; 546/314, 546/315, 332, 333; 549/72; 260/347.8; 548/488

[56] References Cited

U.S. PATENT DOCUMENTS 3,282,875 11/1966 Connolly et al. ............. 260/29.6 F
3,907,837 9/1975 Effenberger et al. ............... 568/323

OTHER PUBLICATIONS

Olah et al., Synthesis, vol. 9, pp. 672-673, (1978).

*Primary Examiner*—Alan L. Rotman
*Attorney, Agent, or Firm*—Jerome Rosenstock

[57] ABSTRACT

A method of preparing substituted acylbenzenes is disclosed. The method comprises reacting selected acylhalides or equivalents with a selected poly-substituted benzene in the presence of an acylating catalyst comprising a perfluoro sulfonic acid polymer.

18 Claims, No Drawings

METHOD OF PREPARING POLY-SUBSTITUTED ACYLBENZENES

BACKGROUND OF THE INVENTION

1. Field of the Invention

This invention relates to a method of preparing poly-substituted acylbenzenes and more particularly to synthesizing these acylbenzenes by means of a perfluoro sulfonic acid polymer acylating catalyst.

2. Discussion of the Prior Art

When an acyl halide or equivalent is reacted with 2-bromo-1, 3-dimethoxybenzene to form the corresponding acylbenzene it has been found that rearrangement products either predominate or at least are present as major contaminants when usual acylating or Friedel-Crafts catalysts are employed. Such rearrangement products involve bromine migration from the 2 to 4 position, e.g.,

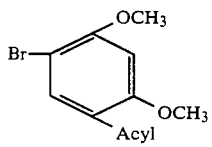

As resported by G. A. Olah, et al., in *Synthesis,* 1978 672, a solid perfluorinated resin sulfonic acid, commercially available from E. I. DuPont de Nemours as Nafion H, can be employed as an acylating catalyst in reactions between acyl halides, anhydrides, or mixtures of acids and their anhydrides and other substituted benzenes. However, it has not heretofore been reported or suggested that such a perfluorinated resin sulfonic acid could function to prevent the formation of rearrangement products when 2-bromo-1,3-dimethoxybenzene is employed.

SUMMARY OF THE INVENTION

The present invention is directed to a method of preparing poly-substituted acylbenzenes and more particularly to synthesizing the acylbenzenes by means of a perfluorosulfonic acid polymer acylating catalyst.

The method comprises reacting a first reactant, selected from

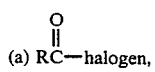

(b) a mixture of

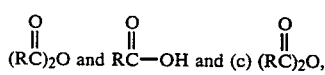

where R is selected from (a') a lower alkyl and (b') a mono or polycyclic aromatic or heteroaromatic having substituents thereon of (X)m and (Y)n, where X and Y are the same or different and are selected from halogen, lower alkyl, lower alkoxy, lower alkylthio, trifluoromethyl and nitro, and m and n are the same or different integers and may vary from 0 to 2, with a second reactant, having a structural formula

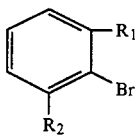

where $R_1$ and $R_2$ are the same or different and are selected from lower alkoxy and hydroxy, in the presence of an acylating agent comprising a perfluorosulfonic acid polymer.

DETAILED DESCRIPTION

The present invention is described primarily in terms of acylating 2-bromo-1,3-dimethoxybenzene to form a substituted benzophenone without essentially forming a contaminating rearrangement acylating product; however, it will be understood that such description is exemplary only and is for purposes of exposition and not for purposes of limitation. It will be readily appreciated that the inventive concept described is equally applicable to acylating 2-bromo-1,3-dimethoxybenzene or 2-bromo-1,3-dihydroxybenzene with any acylhalide or equivalent such as an acylanhydride or mixture of such an anhydride and its corresponding acid.

A first reactant selected from

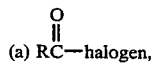

where halogen is selected from fluorine, bromine and chlorine, (b) a mixture of

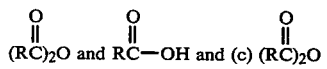

is selected. R is selected from a lower alkyl and a mono or polycyclic aromatic having a substituent thereon of (X)m and (Y)n, where X and Y are the same or different and are selected from halogen, lower alkyl, lower alkoxy, lower alkylthio, trifluoromethyl and nitro, and m and n are the same or different integers and may vary from 0 to 2.

By the term "lower" is meant a substituent having from 1 to 6 carbon atoms. In the case where the desired product is a benzophenone, a benzoyl halide of the formula

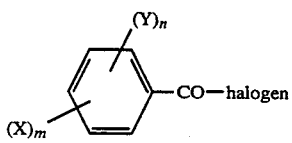

may be selected. Alternatively if a different acylbenzene is desired an opposite first reactant is selected wherein R is lower alkyl, or another appropriately substituted aromatic group or a heteroaromatic group, including but not limited to naphythyl, e.g.,

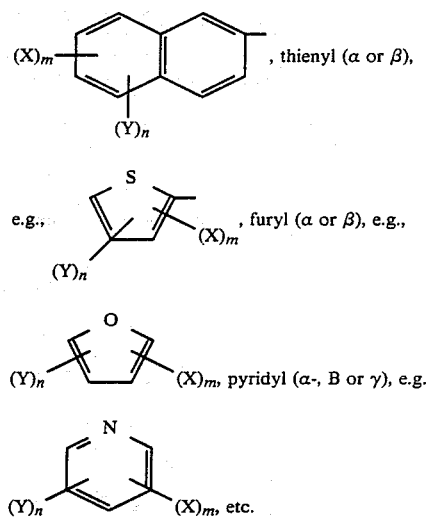

A second reactant comprising a compound of the structure

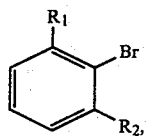

where $R_1$ and $R_2$ are the same or different and selected from lower alkoxy and hydroxy, e.g., 2-bromo-1, 3-dimethoxybenzene, is selected.

A suitable acylating agent or catalyst is selected. A suitable catalyst comprises a perfluorosulfonic acid polymer. Such a polymer comprises a polymeric material obtained from a fluorocarbon vinyl ether having the formula

where $R_f$ is a radical selected from the class consisting of fluorine and perfluoroalkyl radicals having from 1 to 10 carbon atoms, Y is a radical selected from the class consisting of fluorine and the trifluoromethyl radical, n is an integer of 1 to 3 inclusive, and M a radical selected from the class consisting of fluorine, the hydroxyl radical, the amino radical and radicals having the formula—OME where Me is a radical selected from the class consisting of alkali metals and quaternary ammonium radicals. The vinyl ether is readily homopolymerized or copolymerized to form the catalysts of the present invention. Preferred comonomers for copolymerization include ethylene or halogenated ethylenes. It is to be understood, however, the copolymerization of the vinyl/ethers are achieved with any ethylenically unsaturated comonomer capable of homopolyization. Additional fluorinated monomers may also be copolymerized with ethylene or the halogenated ethylenes and the vinyl ethers, such third monomer being for example a perfluoro alpha-olefin, e.g. hexafluoropropylene, or a perfluoro (alkyl vinyl ether) of the type $CF_2=CF-O-[CF_2]n'-CF_3$ where n' is 0 to 5, inclusive.

A preferred catalyst is the group of solid perfluoro sulfonic acid resins or polymers commercially obtained from E. I. DuPont de Nemours and designated as "Nafion" persulfonic acid products. These Nafion products are copolymers of the above-described vinyl ether and tetrafluoroethylene and are supplied in the salt form, e.g., potassium sulfonate. The salt form is readily converted to the acid form by treatment with a mineral acid, e.g. nitric acid, washing with water and drying at 105° C.–110° C. for about twelve hours. The Nafion persulfonic acids have an empirical formula of $[C_7H_{14}O_4SC_2H_4]Z$, where Z is the number of repeated units, and typically have an equivalent weight within the range of 1100 and 1800.

The above perfluorosulfonic acid resins or polymers and their preparation are fully described in Connally et al., U.S. Pat. No. 3,282,875, incorporated by reference hereinto.

The first reactant, the second reactant and the perfluorosulfonic acid polymer catalyst are combined and reacted under the usual Friedel-Crafts reaction conditions. Typically the reactants and catalyst are heated to reflux for a sufficient period of time to achieve the desired acylation, e.g. 22–24 hours.

Surprisingly and unexpectedly, the use of the perfluorosulfonic acid polymer catalyst yields the desired product, 4-acyl-2-bromo-1,3-dialkoxy- or dihydroxybenzene, which is free from contamination or formation of significant rearrangement products. This is a surprising and unexpected result since the usual Friedel-Crafts acylation catalysts, e.g., Lewis acids such as $SnCl_4$, $ZnCl_2$, $AlCl_3$, etc., such rearrangement products are obtained and may often predominate. Such rearrangement products, it is believed, occur because the usual Friedel-Crafts catalysts promote metathesis of the starting material such as 2-bromo-1,3-dimethoxybenzene to yield 4,6-dibromo-1,3-dimethoxybenzene, 2,4-dimethoxybromobenzene and 1,3-dimethoxybenzene. It is this "rearranged starting material" which reacts with the requisite acylating agents to give poor yields of the desired acyl-2-bromo-1,3-dimethoxybenzenes. Surprisingly and unexpectedly the catalysts of the instant process do not cause such rearrangements but promote instead only the desired acylation.

EXAMPLE I

2-Bromo-1,3-dimethoxybenzene [32.60 g; 0.150 mole] and 2-fluorobenzoyl chloride [30.0 g; 0.189 mole] are dissolved in 150 ml of 1,2-dichloro ethane. To this mixture is added ten grams of a copolymer of a fluorocarbon ether of the invention having the general formula

where $R_f$ is a radical selected from the class consisting of fluorine and perfluoroalkyl radicals having from 1 to 10 carbon atoms, Y is a radical selected from the class consisting of fluorine and the trifluoromethyl radical, n an integer of one to three inclusive, and M a radical selected from the class consisting of fluorine, the hydroxyl radical, the amino radical and radicals having the formula —OMe where Me is a radical selected from the class consisting of alkali metals and quaternary ammonium radicals, and tetrafluoroethylene (Nafion H, commercially obtained from E. I. DuPont de Nemours). The reaction mixture is brought to reflux and is stirred. After refluxing for 22 hours the catalyst is filtered off and washed with dichloroethane. The combined organic phase is concentrated under reduced pressure to give crystalline material after trituration with hexane. Recrystallization from isopropanol gives 35.8 grams [70% yield] of 3-bromo-2,4 dimethoxy-2'-fluorobenzophenone, m.p. 88°-91° C., as the sole benzophenone product. After an additional recrystallization from isopropanol, the melting point is raised to 92°-93° C.

ANALYSIS: Calculated for $C_{15}H_{12}BFO_3$: 53.11% C 5.7% H. FOUND: 53.30% C 3.30% H.

EXAMPLE II

For comparison purposes, the procedure of Example I is repeated except that the following Friedel-Crafts acylating agents are employed

[a] $SnCl_4$;
[b] $ZnCl_2$;
[c] $AlCl_3$;
[d] $BBr_3$;
[e] $TiCl_4$.

In all cases, either a desired reaction product is not obtained or a mixture of 3-bromo-2,4-dimethoxy-2'-fluorobenzophenone [desired product], 5-bromo-2,4-dimethoxy-2'-fluorobenzophenone [undesired rearrangement product] and/or the various rearranged starting material as heretofore described is obtained.

The following are comparative procedures for the various catalysts employed which graphically illustrate the surprising and unexpected superiority of the perfluorosulfonic acid polymer catalysts:

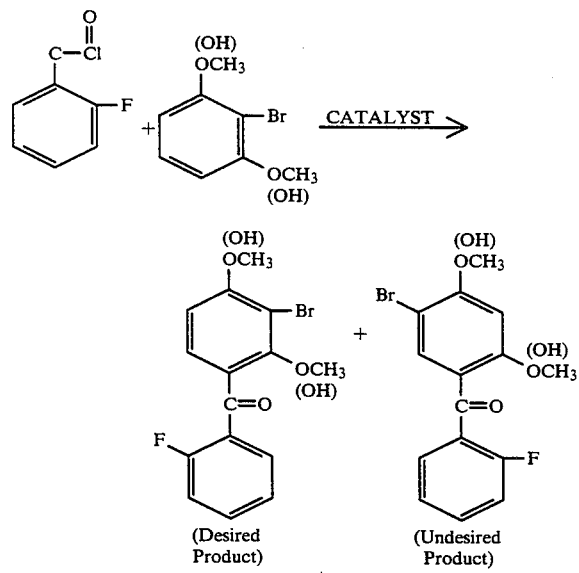

[a] $SnCl_4$

2-Fluorobenzoyl chloride (1.58 g; 0.010 mole) is dissolved in 15 ml of 1,2-dichloroethane at ice bath temperature. Stannic chloride (2.58 g; 0.010 mole) is added and the reaction is stirred 5 minutes, after which 2-bromo-1,3-dimethoxybenzene is added (2.17 g; 0.010 mole) in 3 ml of 1,2-dichloroethane. After 2 hours, the following mixture of products is obtained, as analyzed by the technique of mass spectromotry/gas chromatography: 2-bromo-1,3-dimethoxybenzene (9.5%), 4-bromo-1,3-dimethoxybenzene (trace), 4,6-dibromo-1,3-dimethoxybenzene (8.0%), 2'-fluoro-2,4-dimethoxybenzophenone (11.1%), 3-bromo-2'-fluoro-2,4-dimethoxybenzophenone (22.9%), 5-bromo-2'-fluoro-2,4-dimethoxybenzophenone (13.7%).

[b] $ZnCl_2$ 2-bromo-1,3-dimethoxybenzene (2.17 g; 0.010 mole) is dissolved in 7 ml of dichloromethane and freshly fused zinc chloride (1.36 g; 0.010 mole) is added. After stirring 15 minutes at room temperature, 2-fluorobenzoyl chloride (1.58 g; 0.010 mole) is added. After stirring 3 days at room temperature, the following mixture is obtained, as analyzed by gas chromatography: 2-bromo-1,3-dimethoxybenzene (9%), 4-bromo-1,3-dimethoxybenzene (trace), 4,6-dibromo-1,3-dimethoxybenzene (7%), 2'-fluoro-2,4-dimethoxybenzophenone (22%), 3-bromo-2'-fluoro-2,4-dimethoxybenzophenone (4%), 5-bromo-2'-fluoro-2,4-dimethoxybenzophenone (31%).

[c] $AlCl_3$ 2-bromo-1,3-dimethoxybenzene (217 g; 1.0 mole) and 2-fluorobenzoyl chloride (158 g; 1.0 mole) are dissolved in 1,2-dichorothane and aluminum chloride (133 g; 1,0 mole) is added slowly. The reaction mixture is refluxed for 2 hours and then worked up with 5% hydrochloric acid. In this way a 1:2 mixture of 5-bromo-2'-fluoro-2-hydroxy-4-methoxybenzophenone and 3-bromo-2'fluoro-2-hydroxy-4-methoxybenzophenone is obtained, as indicated by nuclear magnetic resonance (NMR). A quantity of this mixture is separated by preparative high pressure liquid chromatography into its two components, 5-bromo-2'-fluoro-2-hydroxy-4-methoxybenzophenone, m.p. 127°-129° C. and 3-bromo-2'-fluoro-2-hydroxy-4-methoxybenzophenone, m.p. 137°-139° C.

[d] $BBr_3$ 2-bromo-1,3-dimethoxybenzene (4.34 g; 0.020 mole) is dissolved in 15 ml of dichloromethane and 2-fluorobenzoyl chloride (3.16 g; 0.020 mole) is added. This mixture is chilled in an ice bath as boron tribromide is added (3.10 g; 0.020 mole). The reaction is brought to reflux and refluxed 16 hours. Thin layer chromatography shows qualitatively an equal mixture of 5-bromo-2'-fluoro-2-hydroxy-4-methoxybenzophenone and 3-bromo-2'-fluoro-2-hydroxy-4-methoxybenzophenone.

[e] $TiCl_4$ 2-bromo-1,3-dimethoxybenzene (2.17 g; 0.010 mole) and 2-fluorobenzoyl chloride (1.58 g; 0.010 mole) are dissolved in 15 ml of 1,2-dichloroethane at −5° C. and titanium tetrachloride (1.89 g; 0.010 mole) is added. After 2.5 hours gas chromatography shows that 2-bromo-1,3-dimethoxybenzene is entirely consumed and the following mixture of products is present: 4,6-dibromo-1,3-dimethoxybenzene (4%), 2'-fluoro-2,4-dimethoxybenzophenone (10%), 3-bromo-2'-fluoro-2,4-dimethoxybenzophenone (46%), 5-bromo-2'-fluoro-2,4-dimethoxybenzophenone (34%).

EXAMPLE III

As an illustration of the effect that usual Friedel-Crafts catalysts have on the starting 2-bromo-1,3-dimethoxybenzene, 2.17 gm (0.010 mole) of this material is dissolved in 15 ml of 1,2-dichloroethane and ferric chloride (1.62 g; 0.010 mole) is added. After 30 minutes at room temperature gas chromatography shows that 2-bromo-1,3-dimethoxybenzene is almost completely consumed and a mixture of 4-bromo-1,3-dimethoxybenzene, 1,3-dimethoxybenzene, and 4,6-dibromo-1,3-dimethoxybenzene is in its place.

A similar experiment using the perfluorosulfonic acid polymer catalysts of the instant process in place of the ferric chloride affords only unchanged 2-bromo-1,3-dimethoxybenzene.

We claim:

1. A method of preparing a poly-substituted acylbenzene having a structural formula of

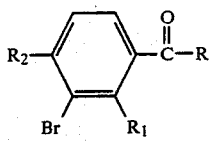

where $R_1$ and $R_2$ are the same or different and are selected from the group consisting of lower alkoxy and hydroxy, R is selected from the group consisting of (a) a lower alkyl, and (b) a mono or polycyclic aromatic or heteroaromatic having substituents thereon of $(X)_m$ and $(Y)_n$ where X and Y are the same or different and are selected from the group consisting of halogen, lower alkyl, lower alkoxy, lower alkylthio, trifluoromethyl and nitro, and m and n are the same or different integers and may vary from 0 to 2, which comprises reacting a first reactant selected from the group consisting of

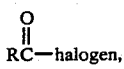
RC—halogen, a mixture of

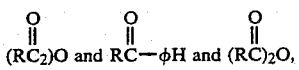
(RC$_2$)O and RC—$\phi$H and (RC)$_2$O, where R is as defined above, with a second reactant having a formula of

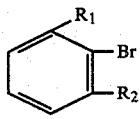

where $R_1$ and $R_2$ are as defined above, in the presence of an acylating agent comprising a perfluorosulfonic acid polymer which is selected from (1) a homopolymer of a vinyl ether having the formula $MSO_2CFR_fCF_2O[CFY_2CF_2O]_nCF=CF_2$ where $R_f$ is a radical selected from the group consisting of fluorine and perfluoralkyl radicals having from 1 to 10 carbon atoms, Y is a radical selected from the group consisting of fluorine and the trifluoromethyl radical, n is an integer of from 1 to 3 inclusive, and M is a radical selected from the group consisting of fluorine, the hydroxyl radical, the amine radical and radicals having the formula —OMe, where Me is a radical selected from the class consisting of alkali metals and quaternary ammonium radicals and (2) a copolymer of the vinyl ether of (1) above and a monomer selected from the group consisting of (a) ethylene, (b) halogenated ethylenes and (c) one monomer selected from ethylene and halogenated ethylenes and one monomer selected from perfluorinated alpha-olefins and perfluoro alkyl vinyl ethers having the formula $CF_2=CF-O-[CF_2]n'CF_3$ where n' is 0 to 5.

2. The method as defined in claim 1 wherein R is selected from the group consisting of phenyl, naphthyl, $\alpha$-thienyl, $\beta$-thienyl, $\alpha$-furyl, $\beta$-Furyl, $\alpha$-pyridyl, $\beta$-pyridyl and $\gamma$pyridyl, each having substituents $(X)_m$ and $(Y)_n$ where X, Y, m and n are as defined.

3. The method as defined in claim 2 wherein R is

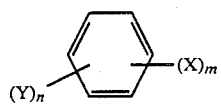

and X, Y, m, n are as defined.

4. The method as defined in claim 1 wherein said vinyl ether is copolymerized with at least a halogenated ethylene.

5. The method as defined in claim 4 wherein said vinyl ether is copolymerized with tetrafluoroethylene.

6. The method as defined in claim 5 wherein said copolymer has a structural formula $(C_7F_{14}O_4S:C_2F_4)_z$ where Z represents a number of repeating units.

7. The method as defined in claim 6 wherein said copolymer has an equivalent weight within the range of 1100 to 1800.

8. The method as defined in claim 1 wherein a 2-fluorobenzoyl halide is reacted with 2-bromo-1,3-dimethoxybenzene to form a reaction product of

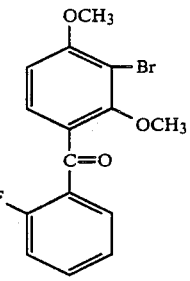

which is essentially free of a rearrangement product.

9. The method as defined in claim 8 wherein said acylating catalyst comprises a copolymer of said vinyl ether and a halogenated ethylene.

10. The method as defined in claim 9 wherein said halogenated ethylene comprises tetrafluoroethylene.

11. The method as defined in claim 10 wherein said copolymer has an empirical formula of $[C_7F_{14}O_4S.C_2F_4]_z$ where Z is the number of repeating units of said copolymer.

12. The method as defined in claim 11 wherein said copolymer has an equivalent weight within the range of 1100 to 1800.

13. The method as defined in claim 1 wherein said catalyst is a copolymer of a vinyl ether having the formula $MSO_2CF_2CF_2OCF(CF_3)CF_2OCF=CF_2$ where M is a radical selected from the class consisting of fluorine, the hydroxyl radical, the amino radical and radicals having the formula —OMe where Me is a radical selected from the class consisting of alkali metals and quarternary ammonium radicals, and tetrafluoroethylene.

14. The method as defined in claim 13 wherein a 2-fluorobenzoyl halide is reacted with 2-bromo-1,3-dimethoxybenzene to form 3-bromo-2,4-dimethoxy-2'-fluorobenzophenone.

15. The method as defined in claim 1 wherein said catalyst is a copolymer of a vinyl ether having a formula $$FSO_2CF_2CF_2OCF[CF_3]CF_2OCF=CF_2$$

and tetrafluoro ethylene.

16. The method as defined in claim 15 wherein a 2-fluorobenzoyl halide is reacted with 2-bromo-1,3-dimethoxy benzene to form 3-bromo-2,4-dimethoxy-2'-fluorobenzophenone.

17. The method as defined in claim 1 wherein said catalyst is a copolymer of a vinyl ether having a formula $$MeOSO_2CF_2CF_2OCF[CF_3]CF_2OCF=CF_2$$

where Me is a radical selected from the class consisting of alkali metals and quaternary ammonium radicals and tetrafluoroethylene.

18. The method as defined in claim 17 wherein a 2-fluorobenzoyl halide is reacted with 2-bromo-1,3-dimethoxybenzene to form 3-bromo-2,4-dimethoxy-2'-fluorobenzophenone.

* * * * *

UNITED STATES PATENT AND TRADEMARK OFFICE
CERTIFICATE OF CORRECTION

PATENT NO. : 4,487,934

DATED : December 11, 1984

INVENTOR(S) : Gregory M. Shutske et al.

It is certified that error appears in the above—identified patent and that said Letters Patent is hereby corrected as shown below:

Claim 1 - line 17: "mono$\overset{O}{\underset{\|}{C}}$r" should be --mono- or $\overset{O}{\underset{\|}{\text{-C-}}}$.--;

Claim 1 - line 33: "...R$\overset{O}{\underset{\|}{C}}$-ØH..." should be --...R$\overset{O}{\underset{\|}{C}}$-OH...--;

Signed and Sealed this

Thirtieth Day of July 1985

[SEAL]

Attest:

DONALD J. QUIGG

Attesting Officer     Acting Commissioner of Patents and Trademarks

UNITED STATES PATENT AND TRADEMARK OFFICE
CERTIFICATE OF CORRECTION

PATENT NO. : 4,487,934

DATED : December 11, 1984

INVENTOR(S) : Gregory M. Shutske, et al.

It is certified that error appears in the above-identified patent and that said Letters Patent is hereby corrected as shown below:

Claim 1 - line 49: "$MSO_2CFR...$" should be --$MSO_2CFR...$--.

Signed and Sealed this

Twenty-fourth Day of September 1985

[SEAL]

Attest:

Attesting Officer

DONALD J. QUIGG

Commissioner of Patents and Trademarks—Designate